United States Patent
Nakamura (10) Patent No.: US 7,735,598 B2
(45) Date of Patent: Jun. 15, 2010

(54) STETHOSCOPE HEAD

(75) Inventor: Shoichi Nakamura, Nagano (JP)

(73) Assignee: ACP Japan Co., Ltd., Tokyo (JP)

( * ) Notice: Subject to any disclaimer, the term of this patent is extended or adjusted under 35 U.S.C. 154(b) by 93 days.

(21) Appl. No.: 10/578,764

(22) PCT Filed: Apr. 19, 2005

(86) PCT No.: PCT/JP2005/007425

§ 371 (c)(1),
(2), (4) Date: Jan. 11, 2008

(87) PCT Pub. No.: WO2006/114863

PCT Pub. Date: Nov. 2, 2006

(65) Prior Publication Data

US 2008/0245602 A1    Oct. 9, 2008

(51) Int. Cl.
*A61B 7/02* (2006.01)
(52) U.S. Cl. ......................... 181/131; 381/67
(58) Field of Classification Search ................. 181/131, 181/137; 381/67
See application file for complete search history.

(56) References Cited

U.S. PATENT DOCUMENTS

| | | | |
|---|---|---|---|
| 4,362,164 A * | 12/1982 | Little et al. | 600/382 |
| 4,502,562 A | 3/1985 | Nelson | |
| 4,770,270 A * | 9/1988 | Grimm | 181/137 |
| 4,802,550 A * | 2/1989 | Poore | 181/131 |
| 4,972,841 A * | 11/1990 | Iguchi | 600/528 |
| 5,252,787 A * | 10/1993 | Moore et al. | 181/131 |
| 5,638,453 A * | 6/1997 | McLaughlin | 381/67 |
| 5,774,563 A * | 6/1998 | DesLauriers et al. | 381/67 |
| 5,812,678 A * | 9/1998 | Scalise et al. | 381/67 |
| 5,910,992 A * | 6/1999 | Ho | 381/67 |
| 5,945,640 A * | 8/1999 | Rossini et al. | 181/131 |
| 6,210,344 B1 * | 4/2001 | Perin et al. | 600/528 |
| 6,244,376 B1 * | 6/2001 | Granzotto | 181/131 |
| 6,342,038 B1 * | 1/2002 | Carrasquillo | 600/500 |
| 2001/0030077 A1 * | 10/2001 | Watson | 181/131 |
| 2004/0114767 A1 * | 6/2004 | Tseng | 381/67 |

FOREIGN PATENT DOCUMENTS

| | | |
|---|---|---|
| EP | 84302101.5 | 3/1984 |
| JP | 54-99390 | 12/1952 |
| JP | 59-183738 | 10/1984 |
| JP | 60-180408 | 11/1985 |
| JP | 3106385 | 10/2004 |

* cited by examiner

*Primary Examiner*—Jeffrey Donels
*Assistant Examiner*—Jeremy Luks
(74) *Attorney, Agent, or Firm*—Michaud-Kinney Group LLP (57) ABSTRACT

A stethoscope is provided with two head portions for fitting two diaphragms different in caliber on a head main portion, having diverse design properties and functions.

A stethoscope head comprising a head main portion and a conduit connecting portion provided on the head main portion, wherein said head main portion comprises a main head portion and a sub-head portion formed from a transparent or semitransparent element formed in the opposite direction each other with the pipe connecting port put therebetween; the main head portion comprises a transparent or semitransparent main diaphragm connected to the conduit connecting port, and the sub-head portion is provided with spaces for receiving the sub-diaphragm for high frequency and or narrow area stethoscope or various functions, and is provided with mounting means for mounting the sub-diaphragm or the apparatus on the sub-head portion.

10 Claims, 12 Drawing Sheets

STETHOSCOPE HEAD

CROSS-REFERENCE TO RELATED APPLICATIONS

This application claims priority to International Patent Application No. PCT/JP2005/007425 filed on Apr. 19, 2005, the subject matter of this patent document is incorporated by reference herein in its entirety.

TECHNICAL FIELD

The present invention relates to a stethoscope head, and particularly, to a stethoscope head in which a head main portion is provided with diaphragms different in caliber, and diversity of design and function is provided.

BACKGROUND ART

Figure 12:
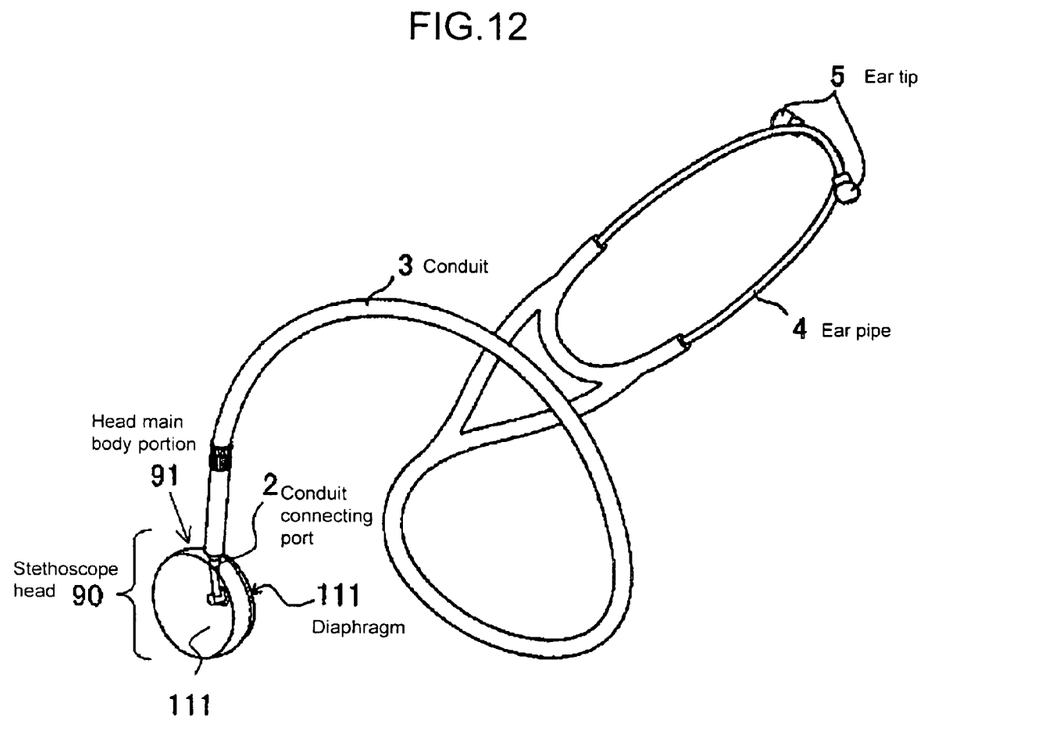
FIG. 12 shows an external view of a conventional stethoscope.

The stethoscope is a medical apparatus used when the health condition of a patient, by listening to a heartbeat sound generated in the body of a patient, is diagnosed or blood pressure is measured, and an example of the form thereof is as shown in FIG. 12. A conventional stethoscope head 90 shown in FIG. 12 comprises a head main body portion 91 for listening to a heartbeat sound of a patient, and a conduit connecting port 2 connected to the head main body portion 91. Further, the conventional stethoscope comprises a conduit 3 connected to the conduit connecting port 2, an ear pipe 4 connected to the conduit 3, and an ear tip installed at the extreme end of the ear pipe 4.

A single diaphragm 111 that functions as a vibration sheet is stretched to the bottom surface of the head main body portion 91. The bottom surface of the diaphragm 111 is placed on the breast of a patient. The heartbeat sound of a patient is transmitted to the diaphragm of the head main body portion 91, and further transmitted via the conduit connecting port 2 secured to the diaphragm 111, the conduit 3, the ear pipe 4, and the ear tip 5, reaching the ear of a doctor having the ear tip inserted therein.

DISCLOSURE OF THE INVENTION

The above-described conventional stethoscope has a problem in that it is designed so that the head main body portion 91 is for an adult, and the caliber of the diaphragm 111 is so large that is not suitable for the bodies of an infant or a child. There is a further problem in that even if a patient is an adult, the stethoscope is not useable to make a diagnosis of a body sound of high frequency included in the heartbeat or the like because of the diameter of the diaphragm.

Further, when the stethoscope is used by a doctor or an attendant, to take blood pressure and pulse or for intravenous feeding, a stop-watch or a metronom device is often also used. Accordingly, there is a need for the functionality of a stop-watch or a metronom device to be provided on the conventional stethoscope.

The present invention has been accomplished in view of the problems as noted above, and there is provided a stethoscope in which a head main body portion is provided with two head portions for fitting two diaphragms different in caliber. Accordingly, even if a patient is an adult, it is possible to make the stethoscope part small in body, or it is possible to make the stethoscope able to monitor high frequency body sound.

A further object of the present invention is to provide a multi-function stethoscope. That is, there is provided a stethoscope in which where a diaphragm having a small caliber is not used, a watch with a stop-watch function is fitted in place of that diaphragm whereby in a functional aspect, time-checking is facilitated, or a liquid-transport metrom is fitted, whereby in a functional aspect, liquid dropping at the time of nurse operation is facilitated, thereby providing enhanced aesthetics to the stethoscope and being excellent in ornament.

SUMMARY OF THE INVENTION

For solving the above-described problem, the present invention provides a stethoscope head comprising a head main body portion and a conduit connecting portion provided on the head main body portion, the head main body portion comprises a main head portion and a sub-head portion formed from a transparent or semitransparent element in the opposite direction from the conduit connecting port positioned therebetween. The main head portion comprises a transparent or semitransparent main diaphragm connected to the conduit connecting port, and the sub-head portion is provided with spaces for receiving a sub-diaphragm for high frequency stethoscope use and or narrow zone stethoscope use or various functions; and there is provided mounting means for mounting the sub-diaphragm or the apparatus on the sub-head portion.

As described above, the sub-head portion of the present stethoscope head is provided with spaces for receiving the apparatus providing various functions, whereby the stethoscope according to the present invention enables providing functions selected out of various functions in addition to the stethoscope.

The above-described mounting means, as an example of its first mounting device, has a detachable elastic member fitted in the outer circumferential edge of the sub-head portion, and a washer member mounted on the outer circumferential edge of the sub-head portion by the elastic ring member to retain the apparatus within the spaces.

The above-described mounting means, as its second mounting device, comprises, a rotatable cam connected to the apparatus, a driving portion to be moved in a horizontal direction by the cam, and an O-ring fitted in the outer circumferential portion of the driving portion. The cam connected to the apparatus is rotated whereby a part of the outer circumferential portion of the driving portion is pressed against the inner wall of a space of the sub-head portion so that the apparatus is mounted on the sub-head portion.

The driving portion has a space for receiving the cam, and the maximum rotational angle of the cam is 90 degrees.

Materials of the main head portion and the sub-head portion can be metal, acryl resin or glass, and the main diaphragm is formed from transparent or semitransparent epoxy resin as elements. However, the present invention is not limited in this regard as other materials known to those skilled in the pertinent art to which the present invention pertains may be substituted without departing from the broader aspects of the present invention.

The stethoscope according to claim 1 wherein the main head portion and the sub-head portion are fitted to each other by a fitting portion.

The apparatus is a stopwatch, a watch, a liquid-transport metrom, a pulse number meter or a thermometer.

The present invention further provides a stethoscope comprising the stethoscope head, a conduit for guiding stethoscope sound connected to the stethoscope head, an ear pipe connected to the conduit, and an ear tip connected to the ear pipe.

As a first form of the stethoscope provided with the stethoscope head, a sub-diaphragm is mounted on the sub-head portion having a conical lid shape. Since this sub-diaphragm is smaller in caliber than that of the normal main diaphragm, the diagnosis adapted to the body of a child can be performed using the sub-head provided with the sub-diaphragm. Further, even if a patient is an adult, it is possible to listen merely to part further narrower than the caliber of the main diaphragm, or to listen to a sound wave higher in frequency.

As a second form of the stethoscope provided with the stethoscope head, an apparatus such as a stop-watch, a watch, a liquid-transport metrom can be attached.

As described above, in the present stethoscope according to the present invention, two diaphragms different in caliber are provided on the head main portion, whereby even if a patient is an adult, the diaphragm smaller in caliber is used to thereby enable listening merely narrow part of the body, and enable a high frequency body sound.

Further, in the present stethoscope head, a stop-watch, a watch, a liquid-transport metrom or the like is selected, and the selected apparatus can be received easily within the space of the conical lid-shaped sub-head portion.

BRIEF DESCRIPTION OF THE DRAWINGS

FIG. 10 explains the structural elements of the mounting device of the present invention, FIG. 10(a), a plan view of a driving portion 1 having a space 4, FIG. 10(b), a side view of the driving portion 1, FIG. 10(c), a plan view of an O-ring, and FIG. 10(d), a plan view of a cam 52, respectively.

FIG. 11(a), shows the state before mounting (fastening) of objects of FIGS. (a), (b), and FIG. 11(b) shows the state after mounting (fastening) of objects of FIGS. (c), (d).

BRIEF DESCRIPTION OF THE PREFERRED EMBODIMENTS

In the following, a plurality of embodiments of the stethoscope according to the present invention will be described in detail with reference to the drawings.

In a first embodiment of the present invention (mounting mode of the sub-diaphragm), a head main body portion formed from a transparent or semitransparent body comprises a main diaphragm (a vibration sheet) provided with two constituent elements (a main diaphragm provided with conventional caliber and a sub-head portion for fitting a sub-diaphragm provided with smaller caliber than conventional caliber, both of which are installed oppositely with a conduit connecting port put therebetween. Further, in the present embodiment, for example, sheets of suitable figures (photograph, picture, comics or the like) can be printed or pasted to the sub-diaphragm having smaller caliber than the conventional caliber.

Figure 1:
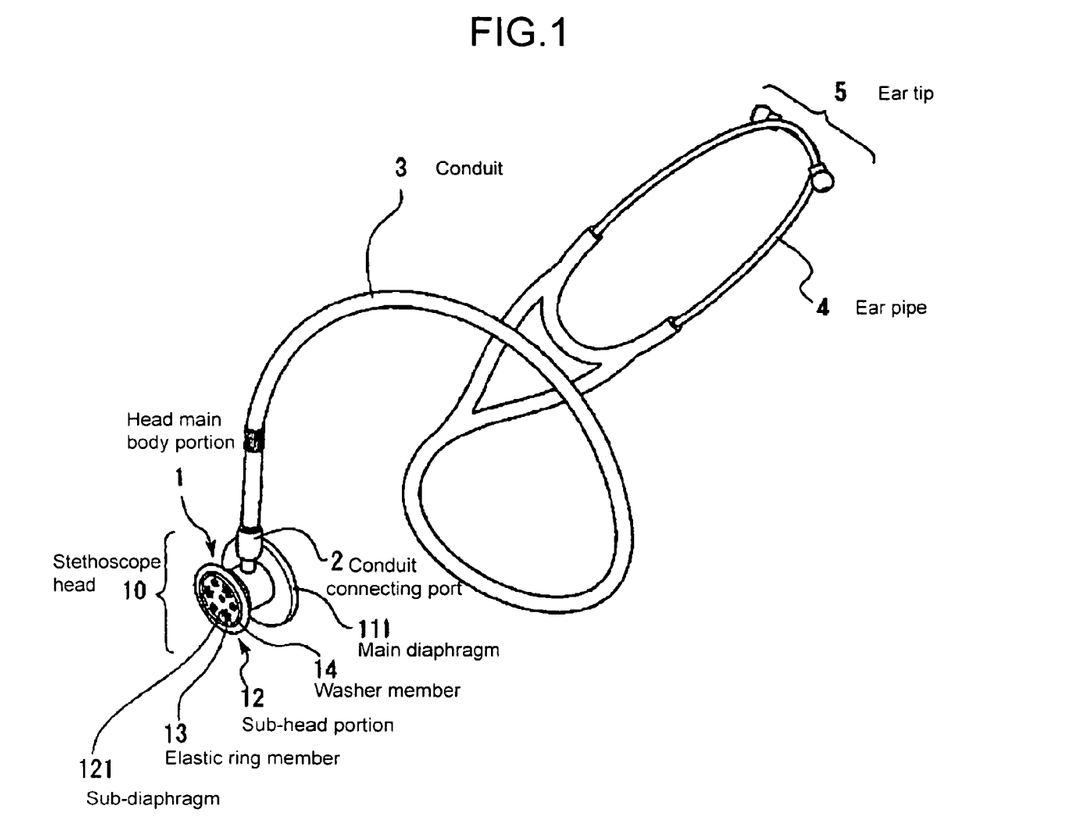
FIG. 1 shows an example of an external view of a stethoscope including a stethoscope head of the present invention.

FIG. 1 shows an example of an external view of the stethoscope including the stethoscope head of the present invention. In the drawing, parts duplicated to those of FIG. 12 are indicated by the same reference numerals. In FIG. 1, a stethoscope head 10 in the present embodiment comprises a head main body portion 1 for listening to a pulse sound of a patient, and a conduit connecting port 2 connected to the head main body portion 1. The whole stethoscope comprises a conduit 3 connected to the conduit connecting port 2, an ear pipe 4 connected to the conduit 3, and an ear tip 5 installed on the extreme end of the ear pipe 4.

The head main body portion 1 comprises a main head portion 11 oppositely with an end of the conduit connecting port 2 put therein, and a sub-head portion 12. In order to stop a sub-diaphragm 111 for high frequency listening and or narrow area listening, and to receive apparatus providing various functions in spaces of the sub-head portion 12 as described later, a detachable elastic ring portion 13 fitted in the outer circumferential portion of the sub-head portion 12 in order to stop the subdiaphragm 111 (the first embodiment) or the apparatus (the second embodiment) is mounted.

Figure 4:
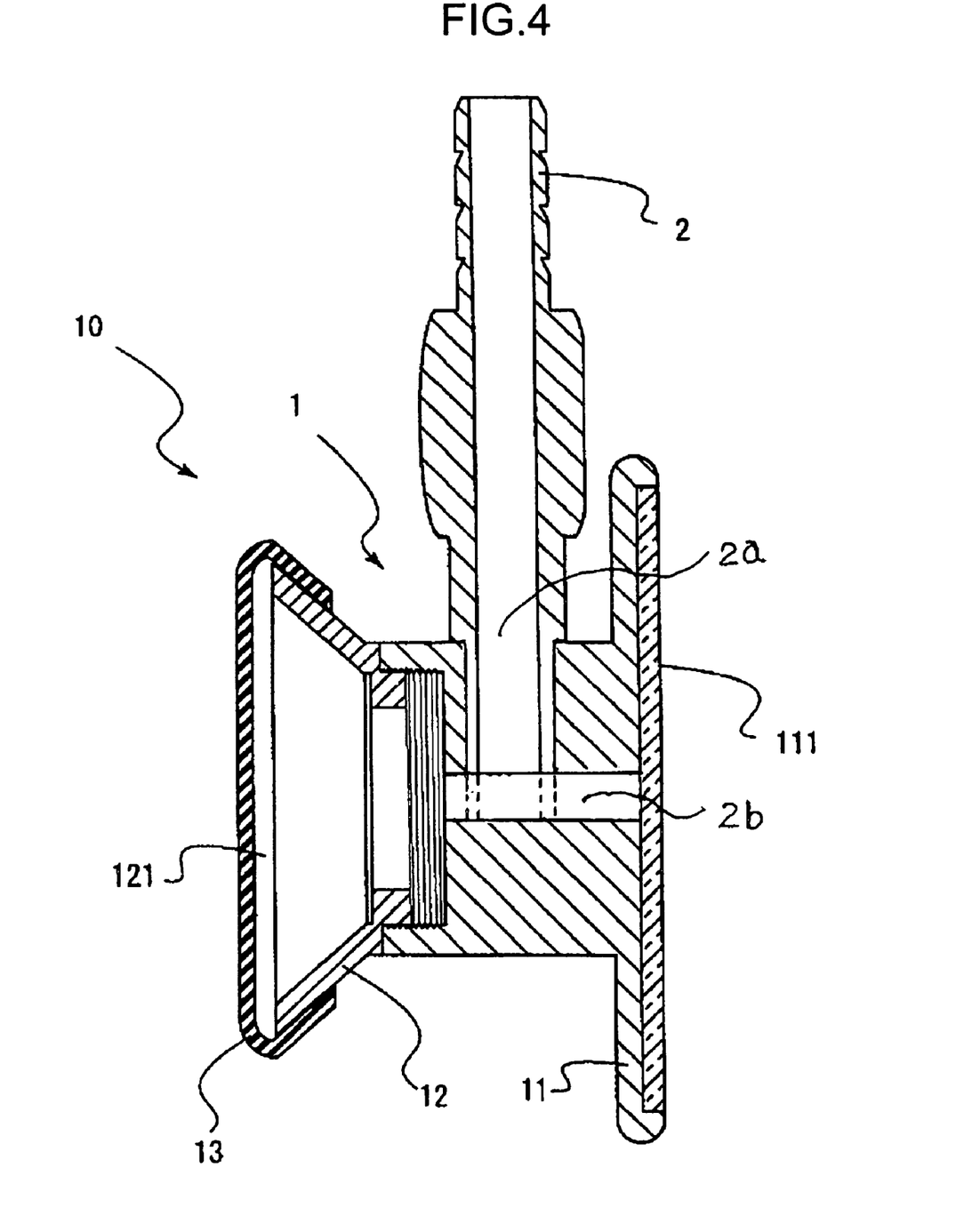
FIG. 4 is an external view showing the structure of a head main body portion of a stethoscope head according to a first embodiment of the present invention.

The main head portion 11 and the sub-head portion 12 of the head main body portion 10 are formed of materials such as transparent or semitransparent acryl, or glass integrally molded or individually molded and fitted as shown in FIG. 4.

Both the main diaphragm 111 and the sub-diaphragm 121 can be formed of transparent or semitransparent epoxy resin or nylon as material. A single main diaphragm 111 to be a vibration sheet is placed on the bottom surface of the main head portion 11. This diaphragm 111 has the same caliber as that of the diaphragm of the conventional stethoscope and the bottom surface thereof is mainly placed on the breast of an adult patient. Further, a single sub-diaphragm 121 to be a vibration sheet is placed on the bottom surface of the sub-head portion 120. This diaphragm 121 has a smaller caliber than that of the diaphragm of the conventional stethoscope and the bottom surface thereof is mainly placed on the breast of an infant patient.

A pulse sound of a patient is transmitted to the main diaphragm 111 or the sub diaphragm 121, passing through a side conduit 2b bored forward of a sound conduit 2a within the conduit 2, further transmitted in order of a conduit connecting port 2, a conduit 3, an ear pipe 4, and an ear tip 5 whose ends are secured to the main diaphragm 111 and the sub diaphragm 121, reaching an ear of a doctor into which the ear tip 5 is inserted. And, the sub-diaphragm 121 is mounted on the sub-head portion 12 by a detachable elastic ring member 13 fitted in the outer circumferential edge of the sub-head portion 12. In FIG. 4, where the main diaphragm 111 is used to listen to a pulse of a patient, for example, the conduit 2 is rotated at predetermined angle with respect to the head main body portion 1 to thereby close the side conduit 2b on the sub-diaphragm 121 side. And, where the main diaphragm 121 is used to listen to a pulse of a patient, the conduit 2 is rotated in the reverse direction at a predetermined angle with respect to the head main body portion 1 to thereby close the side conduit 2b on the main diaphragm 111 side.

Figure 2:
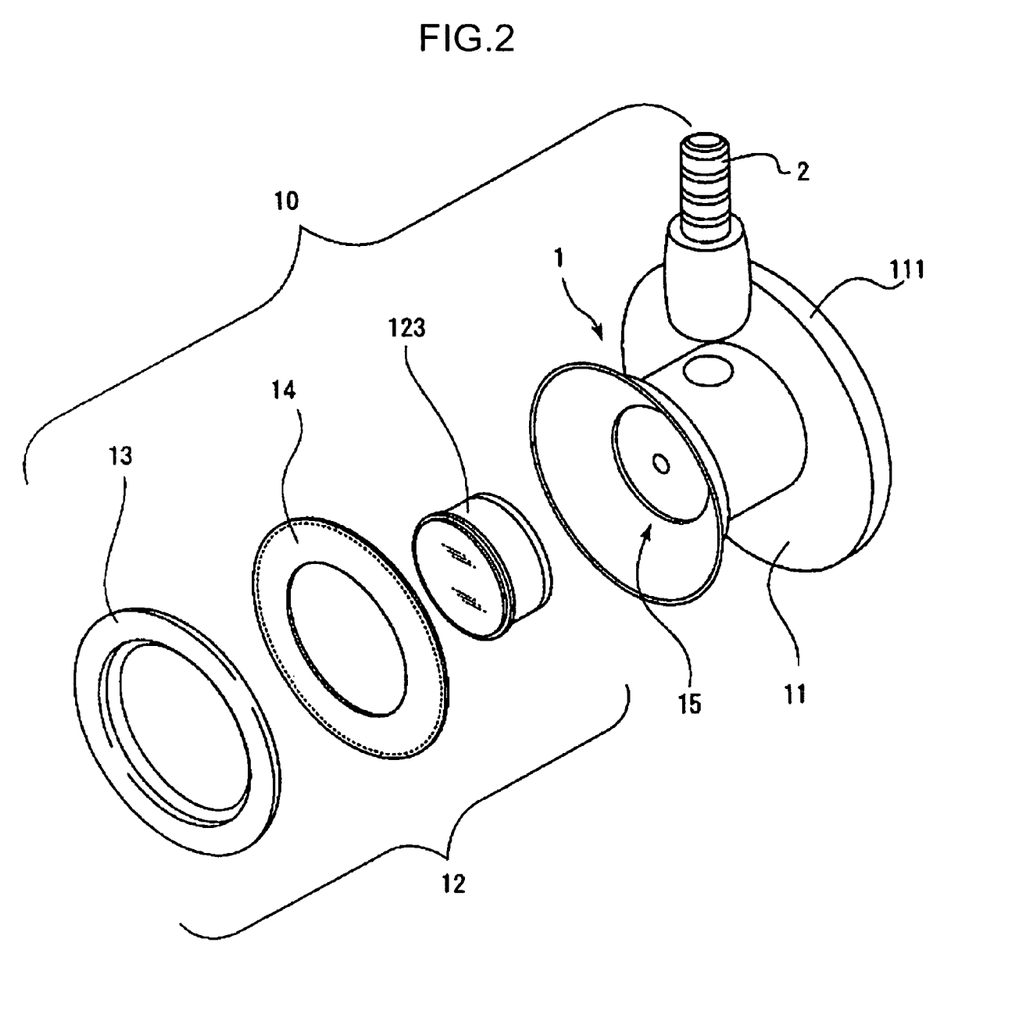
FIG. 2 shows an external view of the whole structure of a stethoscope head of the present invention.

FIG. 2 is a view showing the whole structure according to a second embodiment of the stethoscope head of the present invention for mounting an apparatus 123 in a space 15 within a sub-head portion 12 using a first mounting device. As shown in FIG. 2, the main head portion 11 and the sub-head portion 12 are formed in the reverse direction each other with the conduit connecting port 2 put therebetween. The main head portion 11 and the sub-head portion 12 can be also constituted in which they are individually molded and fitted, even if they are integrally molded.

Further, in case of the structure in which the main head portion 11 and the sub-head portion 12 are individually molded and fitted, they are fitted separately each other in the inner circumferential surface on the sub-head portion 12 side by the head main body portion 11 having a threading portion, as shown in FIG. 4 later.

In the sub-head portion 12, a funnel shaped conical lid portion is constituted, and a trapezoidal conical space 15 is secured internally of the conical lid portion. For example, a watch 123 selected out of various apparatuses can be stored in the space 15, as a second embodiment described later.

In case of receiving apparatuses as a second embodiment of the present invention in the sub-head portion 12 as described, in place of the sub-diaphragm (121 in FIG. 1), a washer member 14 mounted in the outer circumferential edge of the sub-head portion by the elastic ring member 13 to detain a watch 123 within the space 15 is to be used, in addition to the detachable elastic ring member 13 fitted in the outer circumferential edge of the sub-head portion 12. However, the washer member 14 and the apparatus itself such as the watch 123, the liquid-transport metrom or the like may be secured without mounting the elastic ring member 13. In this case, since the washer member 14 and the apparatus are secured to the sub-head portion 12 by screws or fitting means, the elastic ring member 13 is to bear the function for protection for edging the outer circumferential edge of the sub-head portion 12 or ornament.

Figure 3:
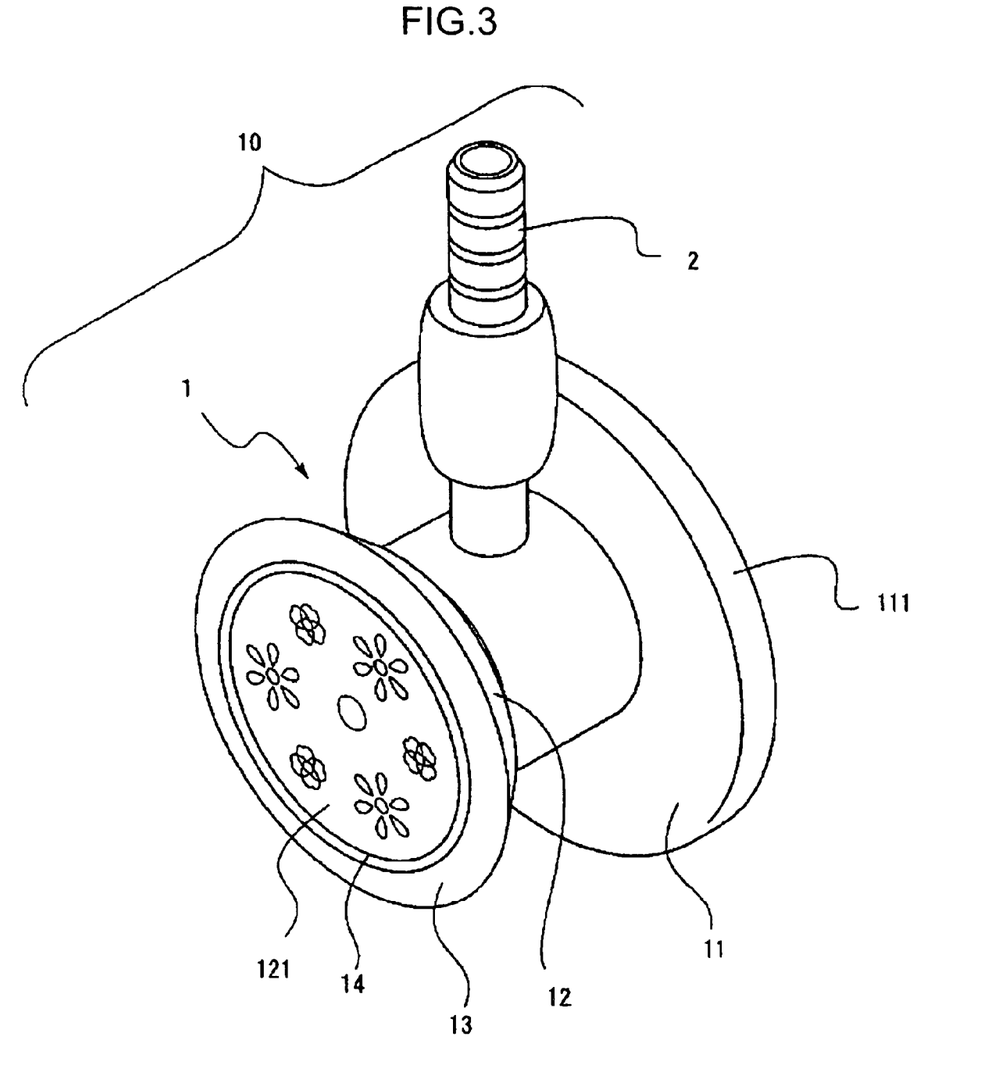
FIG. 3 is an external view showing the structure of a head main body portion of a stethoscope head according to a first embodiment of the present invention.

FIG. 3 is an external view showing the structure of the head main body portion of the stethoscope head according to the first embodiment of the present invention (mounting mode of the sub-diaphragm) according to the present invention. In the embodiment of the present invention shown in FIG. 3, the sub-diaphragm 121 is mounted on the sub-head portion 12 by the elastic ring member 13. In this case, it is not necessary to use the washer member 14 shown in FIG. 2.

FIG. 4 is a sectional view showing one example of the sectional structure of the head main body portion 1 of the stethoscope head according to the first embodiment (mounting mode of the sub-diaphragm) of the present invention. As described above, the head main body portion 1 may be integrally molded, but as shown in FIG. 4, the main head portion 11 and the sub-head portion 12 are fitted separately each other by a method of screwing the sub-head portion having a threading portion in the outer circumferential surface into the head main body portion 1 having a threading portion on the inner circumferential surface on the main head portion 11 side. However, the main head portion 11 and the sub-head portion 12 may be fitted each other by a fitting type fitting portion.

In the second embodiment (mounting mode of the apparatus) of the present invention, the head main body portion formed from a transparent or semitransparent body comprises two structural elements (main head portion and sub-head portion), similar to the aforementioned first embodiment (mounting mode of the sub-diaphragm), both of which are installed to be opposed with the conduit connecting port put therein. However, the main diaphragm is pasted to the main head portion similar to the first embodiment, but a watch with stop-watch function is removably fitted in the sub-head portion in place of the sub-diaphragm. The sub-head having the apparatus such as the watch with stop-watch received therein is removed from the present stethoscope head whereby it can be used as a single watch with stop-watch function.

Figure 5:
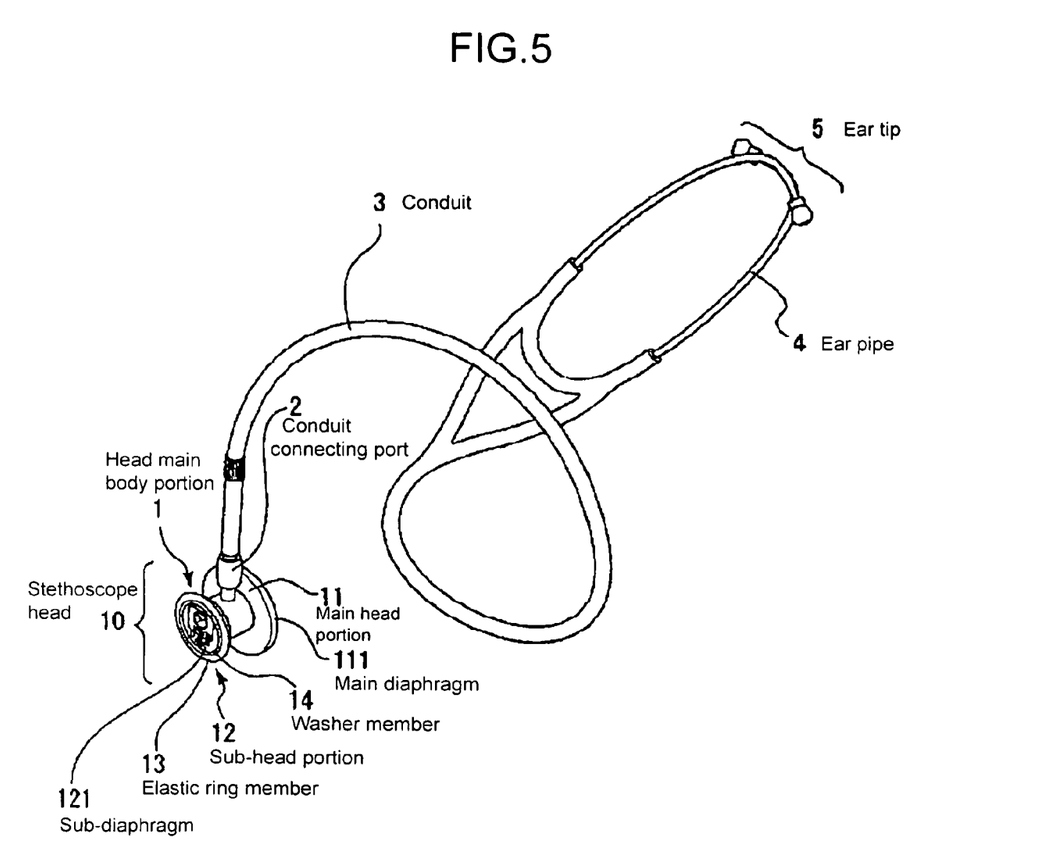
FIG. 5 is an external view of a stethoscope including a stethoscope head in a first example according to a second embodiment of the present invention.

FIG. 5 is an external view of a stethoscope including a stethoscope head according to a second embodiment (mounting mode of apparatus) of the present invention. In this drawing, parts duplicated to FIG. 1 are indicated by the same reference numerals. The stethoscope according to the second embodiment is that in the stethoscope head 10, a watch with stop-watch function 123 as one example of the receivable apparatus, as a structural element in place of the sub-diaphragm 121, is fitted in the sub-head portion 12 of the head main body portion 12. It is noted that as mentioned above, the sub-head having the watch with stop-watch function received therein is removed from the present stethoscope head whereby it can be used as a single watch with stop-watch function.

Figure 6:
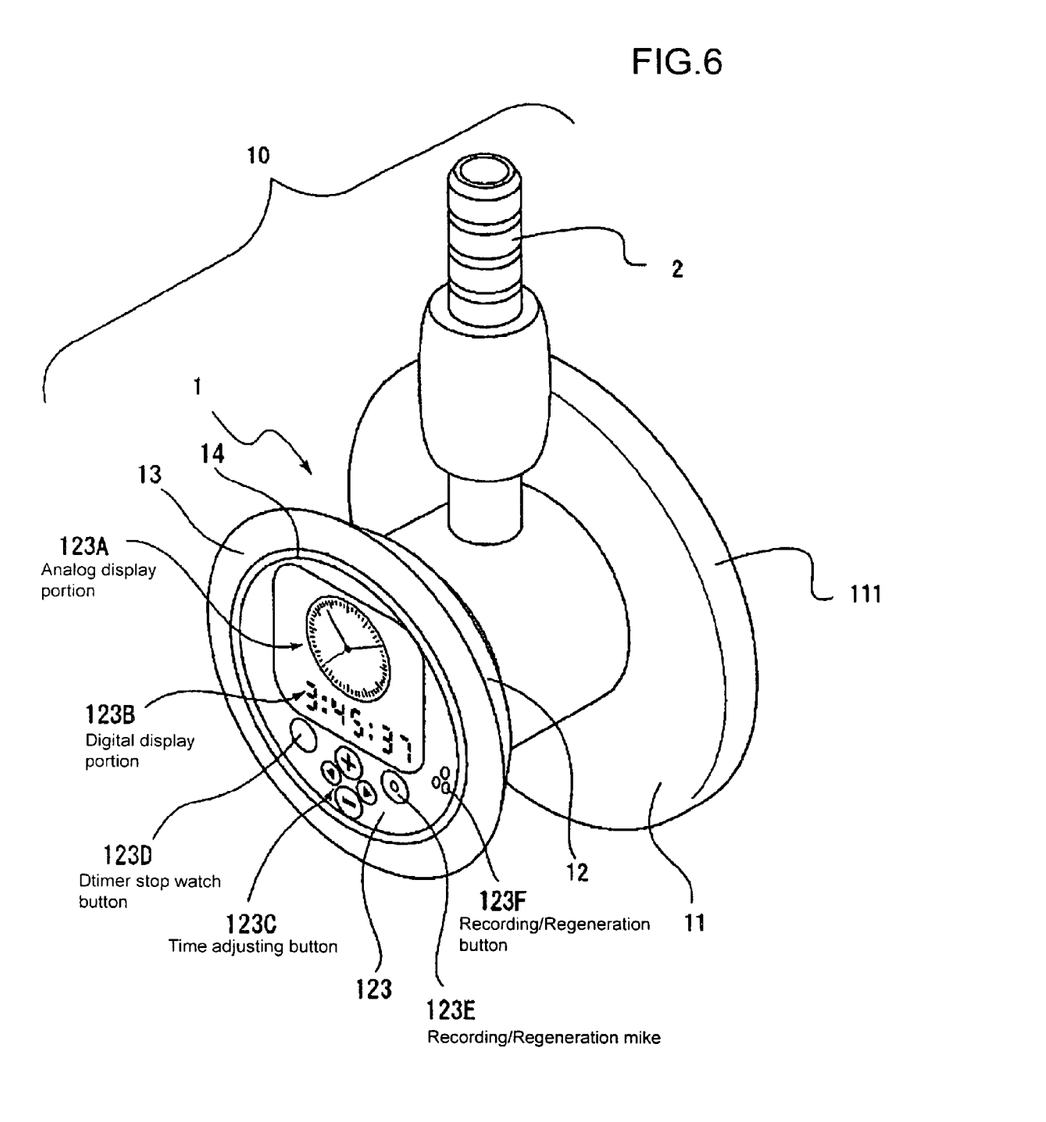
FIG. 6 is an external view showing the structural example of a head main body portion of a stethoscope head in a first example according to a second example of the present invention.

FIG. 6 is an external view showing one structural example of a head main body portion of a stethoscope head according to a second embodiment (mounting mode of apparatus) of the present invention using a first mounting device.

A watch with stop-watch function 123, as a structural element in place of the sub-diaphragm, is fitted in the sub-head portion 12 of the head main body portion 1, as mentioned above.

Because of this, for stopping, for example, the watch with stop-watch function 123 out of the apparatus into the space (15 in FIG. 2) of the sub-head portion, a detachable elastic ring member 13 fitted in the outer circumferential edge of the sub-head portion is mounted. Further, in this case, a washer member 14 mounted in the outer circumferential edge of the sub-head by the elastic ring member 13 to detain the watch with stop-watch function 123 is used. However, as described above, the washer member 14 or the watch with stop-watch function 123 itself may be secured to the sub-head portion 12 without mounting the elastic ring member 13. In this case, the elastic ring member 13 bears function of protection for edging the outer circumferential edge of the sub-head portion 12 or ornament.

In the front surface operating portion of the watch with stop-watch function 123 ate provided an analog display portion 123A for displaying the short hand, the long hand, and the second hand, a digital display portion 123B for displaying time in values showing time, minute and second, a time adjusting button 123C for performing initial setting or adjustment of time, a timer stop watch button 123D, a record/regeneration mike 123E, and a record/regeneration button 123E And, the sub-head having the watch stop watch function received therein is removed from the present stethoscope head whereby it can be used as a single watch with stop watch function.

It is noted, in addition to the above matter, that for enabling use as a pen light during a patrol at night, a white LED can be installed at a suitable position of the front surface operating portion of the watch with stop watch function 123. Further, for preventing erroneous operation during carrying, a key lock button can be installed at a suitable position of the front surface operating portion of the watch with stop watch function 123.

The screen of the watch with stop watch function 123 can be a liquid crystal display screen. Further, the liquid crystal display screen can be one with back light so as to enable listening even at night. Furthermore, the whole outer surface of the watch with stop watch function 123 can be anti-germ specification.

In the timer stop watch 123D, start and stop of time checking can be made by one touch button operation. The record/regeneration mike 123E and the record/regeneration button 123F are used when the record memo is record-regenerated.

Figure 7:
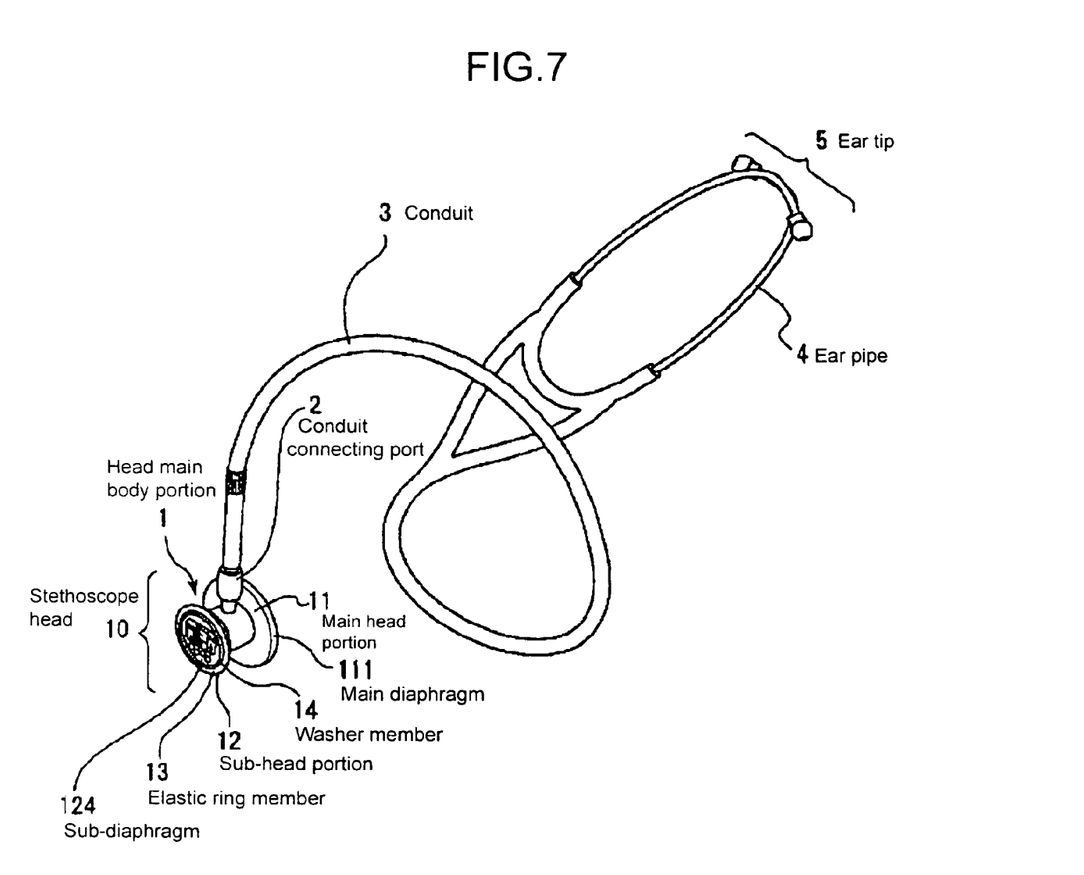
FIG. 7 is an external view of a stethoscope including a stethoscope head in a second example according to a second example of the present invention.

FIG. 7 shows an example in which a liquid-transport metrom 124 is removably fitted in place of the watch with stop watch function 123, in the sub-head portion 12. Also in this case, similarly to the mounting of the watch with stop watch function 123 explained previously, there is mounted the detachable elastic ring portion 13 fitted in the outer circumferential edge of the sub-head portion 12 to be stopped within the space (15 in FIG. 2) of the sub-head portion, and there is used the washer member 14 mounted on the outer circumferential edge of the sub-head portion 12 by the elastic ring member 13 to detain the liquid-transport metrom 124 within the space. However, as described above, the washer member 14 or the liquid-transport metrom itself may be secured to the sub-head portion 12 without mounting the elastic ring member 13, as described above. In his case, the elastic ring member 13 bears the function of protection or ornament for edging the outer circumferential edge of the sub-head portion 12.

Figure 8:
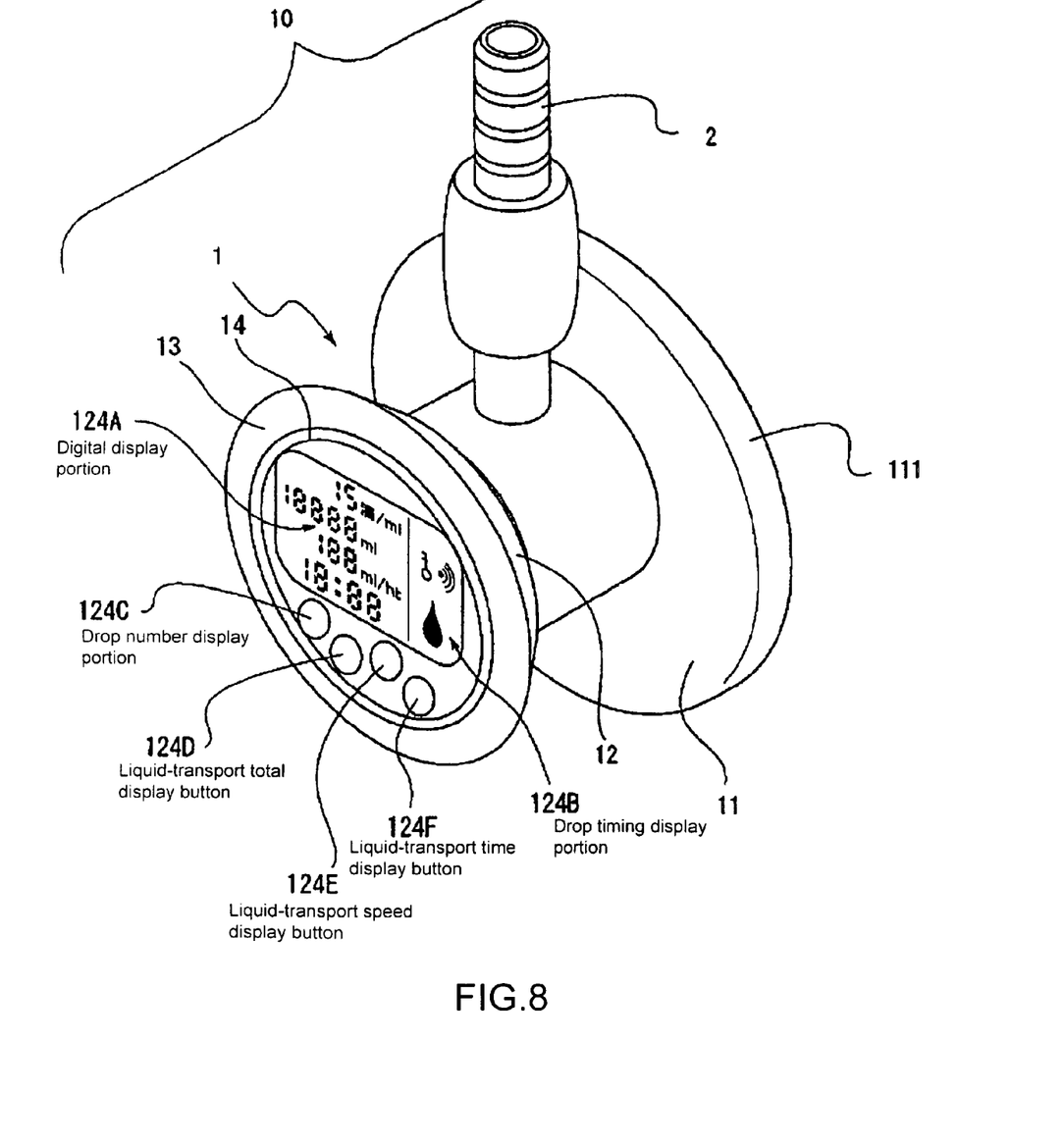
FIG. 8 is an external view showing the structural example of a head main body portion of stethoscope head in a third example of the present invention.

FIG. 8 is an external view showing one structural example of a head main body portion of the stethoscope head where the liquid-transport metrom 124 is fitted. The front surface operating portion of the liquid-transport metrom 124 is provided with a digital display portion 124A for displaying, in numerical values, various data necessary for executing the liquid-transport operation, a drop timing display portion 124B for screen displaying and voice displaying the liquid-transport timing of the liquid-transport operation, a drop-number display button 124C for displaying the liquid-transported drop number, a liquid-transport total display button 124D for displaying the total of liquid-transport, a liquid-transport speed display button for displaying the liquid-transport speed at the time of liquid-transport; and a liquid-transport time display button 124F for displaying liquid-transported time.

It is noted, in addition to the above matter, that a display portion for displaying the total amount of battery can be installed on the digital display portion 124A. Further, for preventing erroneous operation at the time of carrying, a key lock button can be installed at a suitable position of the front surface operating portion of the liquid-transport metrom 124. Further, the whole outer surface of the liquid-transport metrom 124 can be made anti-germ specification.

When the drop number display button 124C is depressed, the liquid-transported drop number is displayed on the liquid-transport drop number display portion of the digital display portion 124A. Further, when the liquid-transport total display button 124D is depressed, the liquid-transport total is displayed on the liquid-transport total number to the digital display portion 124A. Further, when the liquid-transport speed display button is displayed, the liquid-transport speed when liquid-transported is displayed on the liquid-transport speed display portion 11 of the digital display portion 124A. Furthermore, when the liquid-transport time display button 124F is depressed, liquid-transported time is displayed on the liquid-transport time display portion of the digital display portion 124A. And, the sub-head having the liquid-transport metrom received therein is removed from the present stethoscope whereby it can be used as a single liquid-transport storom device.

In the second embodiment (mounting mode of the apparatus) of the present invention, a watch with stop watch function is, as a structural element in place of the sub-diaphragm, fitted in the sub-head portion 12, as previously mentioned, and in the third embodiment of the present invention, the liquid-transport metrom 124 is, as a structural element in place of the sub-diaphragm 121, fitted in the liquid-transport metrom 124. However, other various small elements are fitted in the sub-head portion 12 of the head main body portion 1. Further, as such small elements, a pulse number meter, a thermometer, LED light, and a nurse call buzzer can be fitted in the sub-head portion 12.

The second mounting device in the second embodiment (mounting mode of the apparatus) of the present invention will be described in detail hereinafter.

Figure 9:
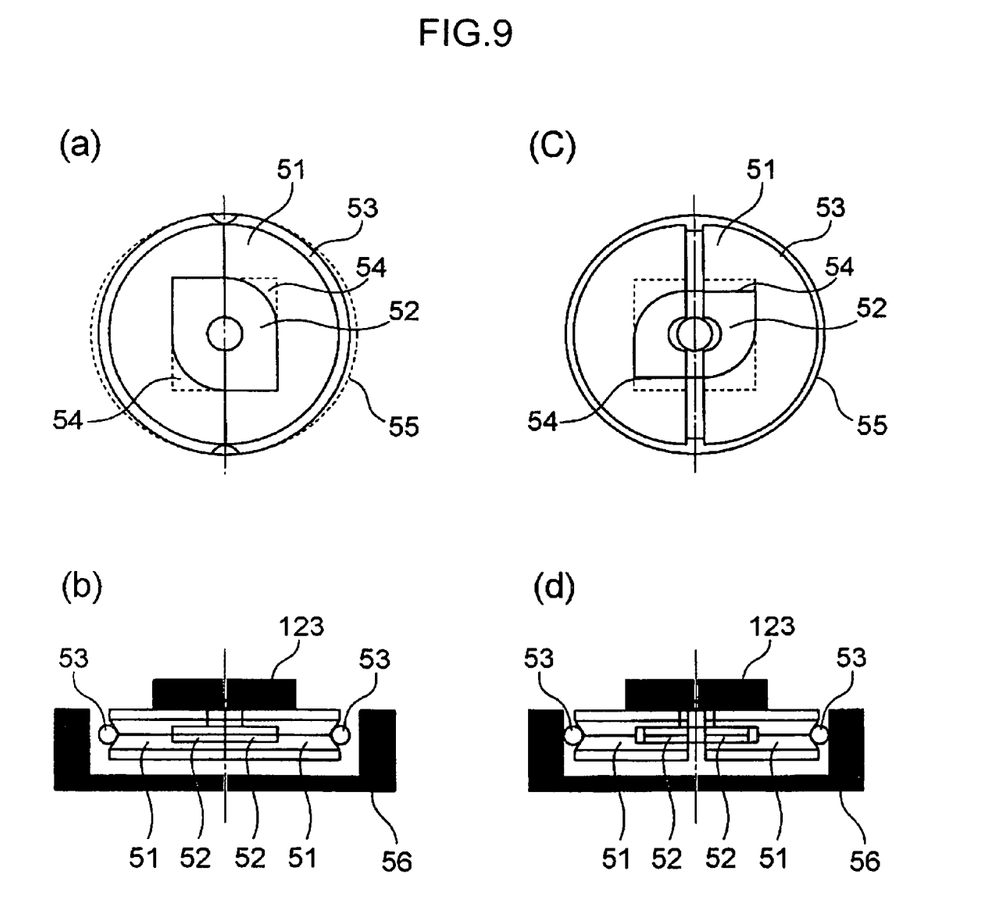
FIG. 9 shows the structure of a mounting device of the present invention, and FIG. 9(a), a plan view of the present mounting device before mounting (fastening) of objects, FIG. 9(b), a sectional view as viewed from the side of the present mounting device before mounting of objects, FIG. 9(c), a plan view of the present mounting device when objects are mounted, and FIG. 9(d), a sectional view as viewed from the side of the present mounting device when objects are mounted, respectively.

FIG. 9 shows the structure of the second mounting device; FIG. 9(b), a sectional view as viewed from the side of the present mounting device before engagement, FIG. 9(c), a plan view of the present mounting device at the time of engagement, and FIG. 9(d), a sectional view as viewed from the side of the present mounting device at the time of engagement.

As shown in FIG. 9, the second mounting device comprises a rotatable cam 52 connected to the apparatus 123, 124, a driving portion 51 which is moved in a horizontal direction by rotation of the cam 52, and an O-ring 53 fitted in the outer circumferential portion of the driving portion 51, and the cam 52 connected to the apparatus 123, 124 is rotated whereby a part of the outer circumferential portion of the driving portion 51 into which the O-ring 53 is fitted is pressed against the inner wall of the space of the sub-head portion 12 so that the apparatus 123, 124 is mounted on the sub-head portion 12. Here, the driving portion 51 has a space for receiving the cam 52, and the maximum rotational angle of the can 52 is formed to be generally 90 degrees.

In FIGS. 9(a) and (c), the second mounting device comprises a driving portion 1 in which left and right semi-circular portions are moved in the direction opposite to each other by rotation of the cam 2, a cam 2 for moving the left and right semi-circular portions in the direction opposite to each other by rotation thereof, an O-ring 3 fitted in the outer circumferential portion of the driving portion 1, and a space 4 for receiving the cam 2.

As shown in FIGS. 9(b) and (d), in the second mounting device, the driving portion 51 having the apparatus 123, 124 mounted thereon are pressed against the inner wall 56 of the space on the sub-head portion 12 through the O-ring 53 to fix it making use of frictional force. Here, as materials constituting the driving portion 51, metal, synthetic resin, water, porcelain, rubber and the like can be used. Further, as materials constituting the cam 52, metal, synthetic resin, water, porcelain and the like can be used. Further, as materials for constituting the O-ring 52, metal, synthetic resin, rubber and the like can be used. It is noted that a spring may well be inserted internally of the O-ring 52 in order to enhance durability.

Figure 10:
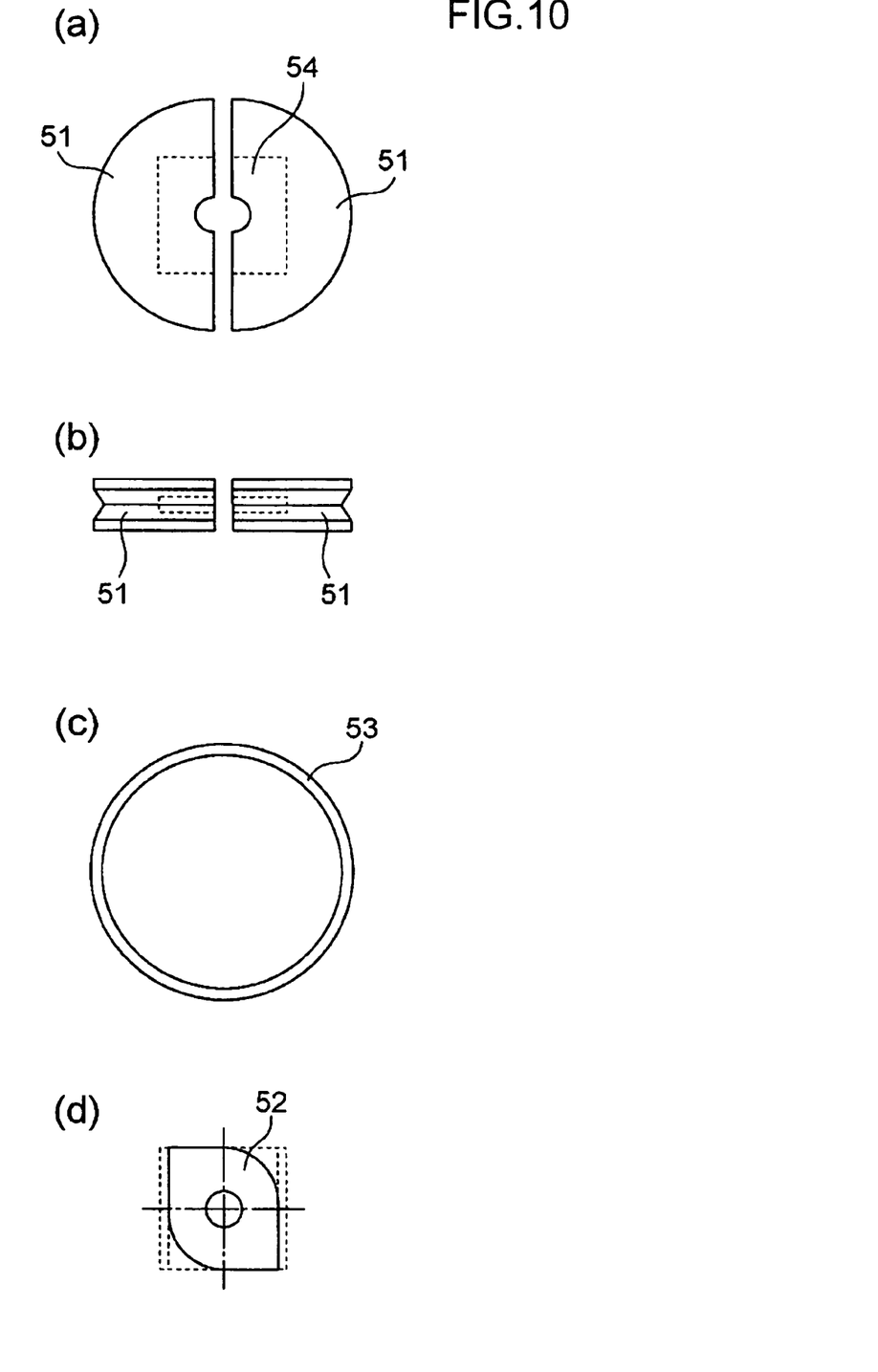

FIG. 10 is an explanatory view for explaining the structural elements of the second mounting device, and FIG. 10(a), a plan view of the driving portion 51 having a space for cam, FIG. 10(*b*), a side view of the driving portion 51, FIG. 10(*c*), a plan view of the O-ring, and FIG. 10(*d*), a plan view of the cam 52, respectively.

In FIG. 10, the driving portion 51 comprises two semicircular portions separated to left and right, and internally thereof is provided a space for cam for receiving a cam 52. In this embodiment, the whole shape of the driving portion 51 (plan view) is generally circular, but in the present invention, generally, the whole shape (plan view) of the driving portion 51 is suitable.

The cam 52 has, as a horizontal line passing through the center, at least two axes (long axis and short axis) different in length, and the cam 52 is constituted so that it can be rotated about the center axis at the maximum angle of 90 degrees (FIG. 9(*a*)). However, when the rotational angle reaches a predetermined angle (for example, 90 degrees), the cam 52 cannot be rotated further. As the cam 52 rotates, the space for cam receiving the cam 52 therein is spread by the action of the long axis. Here, the O-ring has elasticity, and when the outer circumferential portion of the driving portion 51 is expanded along with rotation of the cam 52, it is extended to endure its expansion, and when the outer circumferential portion of the driving portion 51 comes in contact with the inner wall of the space internally of the sub-head portion, the outside diameter of the O-ring 53 which bears a role of a cushion (buffer device) becomes slightly shorter than the inside diameter of the inner wall 56 of the space on the sub-head portion 12 side when engaging the apparatus 123, 124 (before engagement), that is, when the two semi-circular portions of the driving portion 51 are in close contact, because of which when engaged (before engagement), it can be inserted smoothly into the space on the sub-head portion 12 side.

And, the space for cam has a space of the size at the smallest as necessary for receiving the cam 52 when engaging the apparatus 123, 124 (before engagement), that is, when the two semicircular portions of the driving portion 51 are in close contact. When the cam 52 rotates, the space for cam receiving the cam 52 therein is spread, whereby the left and right semi-circular portions of the driving portion 51 having the space for cam move in the direction of moving away each other, because of which in two places of the outer circumferential portion of at least the driving portion 51, the driving portion 51 comes in contact with the inner wall 56 of the space on the sub-head portion 12 side, the contact pressure increases as the cam 52 rotates, and when the rotation of the cam 52 reaches a predetermined rotational angle (for example, 90 degrees), the driving portion 51 is engaged with an internal thread 66 at the maximum strength.

Figure 11:
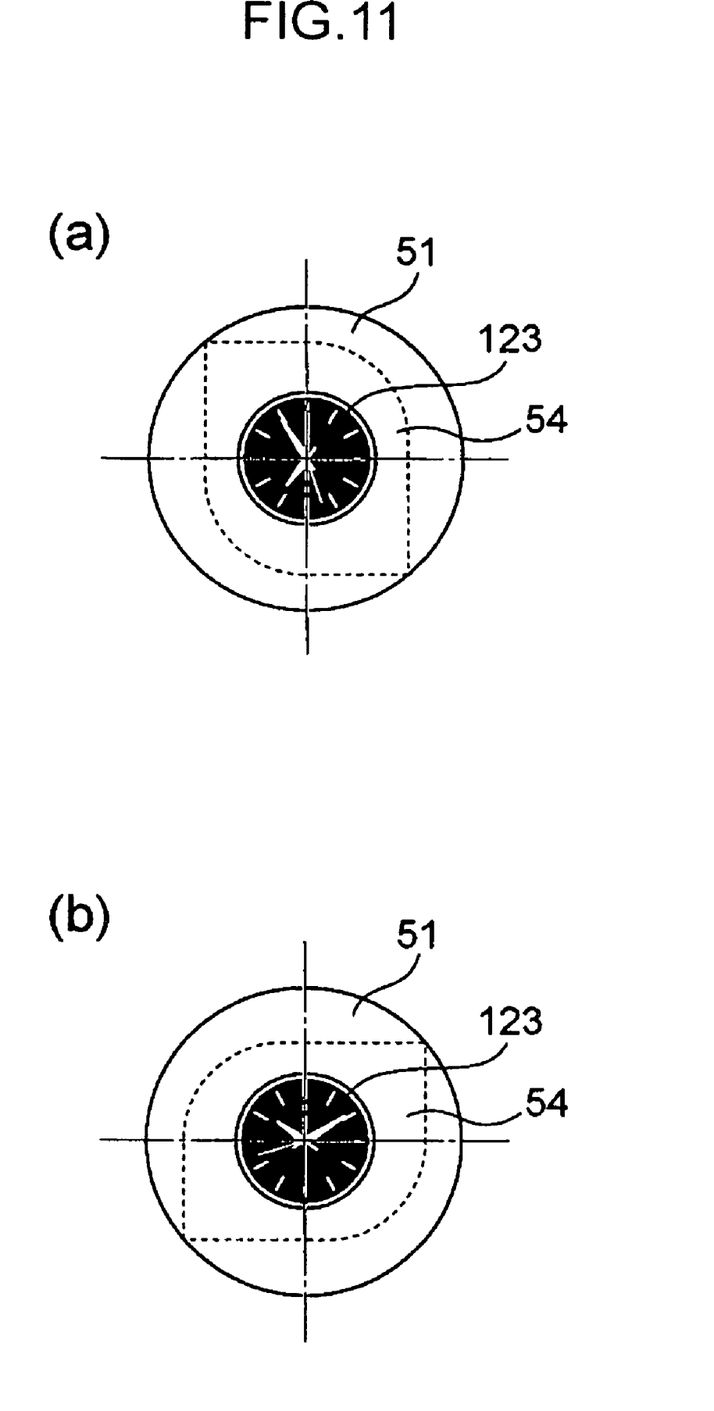
FIG. 11 shows an example in which a watch (apparatus) is mounted using the mounting device of the present invention.

FIG. 11 shows an example in which a watch module (apparatus) 123 is mounted using the second mounting device. FIG. 11(*a*), shows the state before fastening of the watch module 12 corresponding to the state before mounting (fastening) objects in FIGS. 9(*a*) (*b*), and FIG. 11(*c*) shows the state after fastening the watch module 123 corresponding to the state after mounting (fastening) the objects of FIGS. 9(*c*) and (*d*). As described, the angle of the watch 123 is rotated about 90 degrees whereby the mounting device of the present invention is able to fasten or release fastening of the apparatus 123, 124.

As described above in detail, in the stethoscope head of the present invention, two diaphragms different in caliber are provided on the head main body portion, whereby even if a patient is an adult, the diaphragm small in caliber is used to enable listening to mere narrow part on the body or listening to a high frequency body sound. And, in the present stethoscope head, one is selected out of the apparatus such as a stop watch, a watch, or a liquid-transport metrom, and the selected apparatus is received easily into the space of the conical lid shaped sub-head portion to thereby provide the variety of design and function to the stethoscope head.

The invention claimed is:

1. A stethoscope head comprising a head main body portion and a conduit connecting portion provided on said head main body portion,
    said head main body portion including a main head portion and a sub-head portion formed from a transparent or semitransparent element and a conduit connecting port positioned between the main head portion and the sub-head portion,
    said main head portion including a main diaphragm connected to said conduit connecting port,
    said sub-head portion being provided with a space configured for receiving an apparatus; and
    an apparatus including mounting means for mounting said apparatus on said sub-head portion;
    wherein said mounting means comprises a rotatable cam connected to said apparatus, a driving portion to be moved in a horizontal direction by the cam, and an O-ring fitted in the outer circumferential portion of said driving portion,
    the cam being connected to said apparatus and being rotatable whereby a pan of the outer circumferential portion of said driving portion is pressed against the inner wall of a space of the sub-head portion so that said apparatus is mounted on said sub-head portion.

2. The stethoscope head according to claim 1, wherein said sub-head portion has an outer circumferential edge and the mounting means has a detachable elastic member fitted in said outer circumferential edge.

3. The stethoscope head according to claim 2, further comprising a washer member mounted on the outer circumferential edge of the sub-head portion by the elastic ring member to retain the apparatus within said space.

4. The stethoscope head according to claim 1, wherein said driving portion has a space for receiving said cam.

5. The stethoscope head according to claim 4, wherein the maximum rotational angle of said cam is 90 degrees.

6. The stethoscope head according to claim 1, wherein said main head portion and said sub-head portions are formed from at least one of metal, acryl resin or glass.

7. The stethoscope head according to claim 1, wherein said main diaphragm is formed from a transparent or semitransparent epoxy resin or nylon.

8. The stethoscope head according to claim 1, wherein said main head portion and said sub-head portion are constructed such that they are fitted to each other by a fitting type fitting portion.

9. The stethoscope head according to claim 1, wherein said apparatus is a stop-watch, a watch, a liquid-transport metrom, a pulse meter or a thermometer.

10. A stethoscope comprising a stethoscope head according to claim 1, wherein said stethoscope head includes a conduit for guiding a stethoscope sound connected to said stethoscope head, an ear pipe connected to said conduit, and an ear tip connected to said ear pipe.

* * * * *

UNITED STATES PATENT AND TRADEMARK OFFICE
CERTIFICATE OF CORRECTION

| | | |
|---|---|---|
| PATENT NO. | : 7,735,598 B2 | Page 1 of 1 |
| APPLICATION NO. | : 10/578764 | |
| DATED | : June 15, 2010 | |
| INVENTOR(S) | : Nakamura | |

It is certified that error appears in the above-identified patent and that said Letters Patent is hereby corrected as shown below:

In Claim 1
Column 2, line 28: After "whereby a", please delete "pan" and substitute --part--.

Signed and Sealed this

Fourteenth Day of September, 2010

David J. Kappos
*Director of the United States Patent and Trademark Office*